US006665370B2

(12) United States Patent
Bruder et al.

(10) Patent No.: US 6,665,370 B2
(45) Date of Patent: Dec. 16, 2003

(54) COMPUTED TOMOGRAPHY METHOD AND APPARATUS FOR ACQUIRING IMAGES DEPENDENT ON A TIME CURVE OF A PERIODIC MOTION OF THE SUBJECT

(75) Inventors: Herbert Bruder, Hoechstadt (DE); Thomas Flohr, Uehlfeld (DE); Robert Mayer, Erlangen (DE); Bernd Ohnesorge, Erlangen (DE); Stefan Schaller, Fuerth (DE); Karl Stierstorfer, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 10/191,628

(22) Filed: Jul. 9, 2002

(65) Prior Publication Data

US 2003/0072419 A1 Apr. 17, 2003

(30) Foreign Application Priority Data

Jul. 9, 2001 (DE) .......................... 101 33 237

(51) Int. Cl.$^7$ ................................ A61B 6/03
(52) U.S. Cl. ................ 378/15; 378/8; 378/94
(58) Field of Search ................ 378/4, 8, 15, 901

(56) References Cited

U.S. PATENT DOCUMENTS

| | | | |
|---|---|---|---|
| 5,802,134 A | | 9/1998 | Larson et al. |
| 5,881,122 A | * | 3/1999 | Crawford et al. ............ 378/4 |
| 5,887,047 A | * | 3/1999 | Bailey et al. ............ 378/4 |
| 5,909,477 A | * | 6/1999 | Crawford et al. ............ 378/4 |
| 6,130,929 A | * | 10/2000 | Saha ............ 378/4 |

FOREIGN PATENT DOCUMENTS

DE 198 42 238 4/2000

OTHER PUBLICATIONS

K. Taguchi et al., "Algorithm for Image Reconstruction in Multi–Slice Helical CT", Med. Phys. 25, pp. 550–561, 1998.

H. Hu, "Multi–Slice Helical CT: Scan and Reconstruction", Med. Phys, 26, pp. 5–18, 1999.

S. Schaller et al., "New, Efficient Fourier–Reconstruction Method for Approximate Image Reconstruction in Spiral Cone–Beam CT at Small Cone–Angles," SPIE Medical Imaging Conf., Proc. vol. 3032, pp. 213–224, 1997.

S. Schaller., "Exact Radon Rebinning Algorithm for the Long Object Problem in Helical Cone–Beam CT", IEEE Transactions on Medical Imaging, vol. 19, No. 5, pp. 361–375, May 2000.

K. Kudo et al., "Cone–Beam Filtered Back–Projection Algorithm for Truncated Helical Data", in Phys. Med. Biol., 43, pp. 2885–2909, 1998.

* cited by examiner

*Primary Examiner*—David V. Bruce
(74) *Attorney, Agent, or Firm*—Schiff Hardin & Waite

(57) ABSTRACT

In a spiral scan cone beam computed tomography method and apparatus, the output data are divided into sub-segments being shorter than the length required for the reconstruction of a CT image. Segment images having inclined image plane relative to the system axis are reconstructed for the sub-segments. A signal reproducing the time curve of the periodic motion is acquired during the scanning. A z-position on the system axis and a time position with respect to the periodic motion are allocated to the segment images. Segment images belonging to a desired range of z-positions and a desired range of time positions are selected such that the corresponding sub-segments have an overall length adequate for the reconstruction of a CT image. The selected segment images are at least indirectly combined into a resulting CT image with respect to a target image plane.

80 Claims, 6 Drawing Sheets

COMPUTED TOMOGRAPHY METHOD AND APPARATUS FOR ACQUIRING IMAGES DEPENDENT ON A TIME CURVE OF A PERIODIC MOTION OF THE SUBJECT

BACKGROUND OF THE INVENTION

1. Field of the Invention

The present invention is directed to a method and apparatus for computed tomography.

2. Description of the Prior Art

A computed tomography method is known wherein, a subject is scanned with a conical ray beam emanating from a focus and with a matrix-like detector array for detecting the ray beam, with the focus being moved on a spiral path around a system axis relative to the subject, and the detector array supplies output data corresponding to the received radiation, and wherein images of an object region executing a periodic motion are reconstructed from output data respectively supplied during the motion of the focus on a spiral segment, the images being reconstructed dependent on the time curve of a signal that is acquired during the scanning that reflects the time curve of the periodic motion.

A computed tomography (CT) apparatus also is known having a radiation source with a focus from which a conical ray beam emanates, a matrix-like detector array for detecting the ray beam, which supplies output data corresponding to the received radiation, means for generating a relative motion between the radiation source/detector array and a subject, on the other hand, and an image computer to which the output data are supplied, wherein the means for producing a relative motion for scanning the subject produce a relative motion of the focus with respect to a system axis such that the focus moves on a helical spiral path relative to the system axis, the middle axis of the spiral path corresponding to the system axis, a device for obtaining a signal during the scanning which represents the time curve of the periodic motion, and an image computer that reconstructs images of an object region executing the periodic motion from the detector output data respectively and the periodic motion signal.

German OS 198 42 238 discloses such a method and apparatus. A disadvantage of this method is that it is suited only for detector arrays having a relatively small extent in the direction of the system axis.

Various CT methods making use of a conical X-ray beam are known, particularly in conjunction with detectors having several lines of detector elements. The cone angle that occurs as a consequence of the conical shape of the X-ray beam is thereby taken into account in different ways.

In the simplest case (see, for example, B. K. Taguchi, H. Aradate, "Algorithm for image reconstruction in multi-slice helical CT", Med. Phys. 25, pp 550–561, 1998; H. Hu, "Multi-slice helical CT: Scan and reconstruction", Med. Phys. 26, pp. 5–18, 1999), the cone angle is left out of consideration, with the disadvantage that artifacts occur given a large number of detector lines, and thus a large cone angle.

Further, an algorithm referred to as the MFR algorithm (S. Schaller, T. Flohr, P. Steffen, "New, efficient Fourier-reconstruction method for approximate image reconstruction in spiral cone-beam CT at small cone-angles", SPIE Medical Imaging Conf., Proc. Vol. 3032, pp. 213–224, 1997) is known. A disadvantage of this method is that a complicated Fourier reconstruction is needed and the image quality leaves something to be desired.

Exact algorithms also have been disclosed (see, for example, S. Schaller, F. Noo, F. Sauer, K. C. Tam, G. Lauritsch, T. Flohr, "Exact Radon rebinning algorithm for the long object problem in helical cone-beam CT", in Proc. of the 1999 Int. Meeting on Fully 3D Image Reconstruction, pp. 11–14, 1999 or H. Kudo, F. Noo and M. Defrise, "Cone-beam filtered backprojection algorithm for truncated helical data", in Phys. Med. Biol., 43, pp. 2885–2909, 1998), these having the common disadvantage of an extremely complicated reconstruction.

A method and CT apparatus of the type initially described also are disclosed in U.S. Pat. No. 5,802,134. As disclosed therein, images are reconstructed for image planes that are inclined relative to the system axis z by an inclination angle $\gamma$ around the x-axis. As a result, the (at least theoretical) advantage is achieved of the images containing fewer artifacts when the inclination angle $\gamma$ is selected such that a good, optimum adaptation of the image plane to the spiral path is established, insofar as possible according to a suitable error criterion, for example the minimum quadratic average of the distance of all points of the spiral segment from the image plane as measured in the z-direction.

In the case of U.S. Pat. No. 5,802,134, fan data—i.e. data registered using known fan geometry—that were acquired given the motion of the focus over a spiral segment having the length 180° plus fan angle, for example 240°, are thereby employed for the reconstruction. The optimum inclination angle $\gamma$ is dependent on the slope of the spiral, and on the pitch p.

The method disclosed in U.S. Pat. No. 5,802,134 can be employed for arbitrary values of the pitch p. An optimum utilization of the available detector area and thus of the radiation dose applied to the patient for image acquisition (detector and, thus, dose utilization), however, is not possible below a maximum pitch $p_{max}$. This is because even though a given transverse slice, i.e. a slice of the subject residing at a right angle relative to the system axis z, that is longer than 180° plus fan angle is scanned over a spiral segment, only a spiral segment of the length 180° plus cone angle can be used for values of the pitch p below the maximum pitch $p_{max}$, since the use of a longer spiral segment would make it impossible to adapt the image plane adequately well to the spiral path.

SUMMARY OF THE INVENTION

An object of the present invention is to provide a method and a CT apparatus of the type initially described which are also suited, i.e. enable high-quality images, for detector arrays having a large extent in the direction of the system axis.

The above object is achieved in accordance with the invention in a computed tomography method and apparatus wherein a subject having a subject with a conical ray beam emanating from a focus and with a matrix-like detector array for detecting the ray beam, while the focus is moved on a spiral path around a system axis relative to the subject, and the detector array supplies output data corresponding to the received radiation. The output data respectively supplied during the motion of the focus on a spiral segment and having a length adequate for the reconstruction of a CT image are divided into output data with respect to sub-segments, with the length of each sub-segments being shorter than the length required for the reconstruction of a CT image. Segment images having an inclined image plane relative to the system axis are reconstructed for the sub-segments. A signal reproducing the time curve of the periodic motion is acquired during the scanning. A z-position on the system axis and a time position with respect to the periodic motion are allocated to the segment images. Segment images belonging to a desired range of z-positions and a desired range of time positions are selected such that the corresponding sub-segments have an overall length adequate for the reconstruction of a CT image. The selected segment images are at least indirectly combined into a resulting CT image with respect to a target image plane.

In the invention, the cone angle is taken into consideration since sub-segments are first formed and segment images are reconstructed with respect to the sub-segments, the deviations of the image areas from the spiral path along the sub-segments being very small for these segment images since the length of each sub-segment is shorter than the length required for the reconstruction of a CT image. The segment images thus contain only very slight deviations of the image areas of the segment images from the spiral path along the sub-segments, so that the image quality in the generation of the resulting CT image is high even given a large number of detector lines.

Since the segment images have a z-position on the system axis and a time position with respect to the time curve of the periodic motion allocated to them, it is easily possible in the invention to select only those segment images for compilation into a resulting CT image of a desired target image area that lie in a desired range in view of their z-position as well as in view of their time position. It must be assured that the sub-segments belonging to the selected segment images exhibit an overall length that suffices for the reconstruction of a CT image (for example, 180° plus fan angle).

Whereas the method disclosed in German OS 198 42 238 is suitable for multi-line detectors having up to a maximum of approximately ten through twelve lines of detector elements (based on a width of a line of detector elements of 1 mm measured in the direction of the system axis), the inventive method (based on the same width of a line of detector elements) supplies high-quality images even given an extremely large number of lines of, for example, sixty four lines.

According to one version of the invention, the selected segment images belong to sub-segments derived from a single phase of the periodic motion, again with the overall length of the sub-segments being sufficient for the reconstruction of a CT image.

Alternatively, the selected segment images can belong to sub-segments derived from a number of phases of the periodic motion, with the overall length of the sub-segments being sufficient for the reconstruction of a CT image. This procedure offers the advantage of a higher time resolution, this being achieved by the use of sub-segments of the same motion phase in successive phases of the periodic motion (for example, heartbeats) for the reconstruction. These sub-segments correspond to a narrower time window.

Fundamentally, there is the possibility of combining the selected segment images directly to form the resulting CT image, this being particularly simple when the target image area corresponds to the z-position of the selected segment images. Insofar as the z-positions of the selected segment images differ from the target image area, the segment images in one version of the invention are reformatted onto the target image area before being combined into the resulting CT image. This can be accomplished, for example, by interpolation.

According to one version of the invention, the selected segment images are directly combined to form the resulting CT image by the selected segment images belonging to a sub-segment being combined into a sub-image (or partial image) with respect to the target image area, before the sub-images are combined into a resulting CT image.

For imaging a volume, in an embodiment of the invention CT images of successive subject slices in the direction of the system axis are generated. The successive subject slices should adjoin one another for producing a gap-free presentation of the volume.

The pre-requisites for an optimum detector, and thus dose utilization, are also established in the invention for values of the pitch p below the maximum pitch $p_{max}$. In order to have data available for a gap-free presentation of a volume, however, the maximum pitch $p_{max}$ cannot be utilized without further measures. The slope of the spiral path must be limited, for example in the way disclosed in German OS 198 42 238, such that the sub-volumes reconstructed in every cycle of the periodic motion fit each other gap-free.

So that the feed is not excessively limited, in a version of the invention the image areas of the segment images are not planar but are curved, for enlarging the volume acquired with the segment images belonging to a sub-segment.

If it should occur that the feed was selected too large, repetition of the examination can be avoided by the missing segment images being calculated by interpolation from segment images from the preceding or following period of the motion, dependent on the desired z-positions and time positions.

The maximum inclination of the image surfaces of the segment images is determined from weighting for the image area of each segment image must be present at both ends of a sub-segment within the measurement field.

The segment images, which are unusable by themselves because of the fact that that the length of each sub-segment is shorter than the length required for the reconstruction of a CT image, are calculated in a known way, i.e. the rays that are most beneficial for the image area of the respective segment image are selected from the projections for the respective sub-segment in parallel or fan geometry according to a suitable error criterion, and are filtered and back-projected, or reconstructed with another standard method.

A useable image arises only given the direct or indirect combination o the selected segment images to form a resulting CT image, i.e. given reformatting onto the target image area.

The image quality of this image is especially high when the segment images are reconstructed for image planes that are inclined around a first axis intersecting the system axis at a right angle by an inclination angle $\chi$ as well as around a second axis intersecting each of the first and the system axis at a right angle by a tilt angle $\delta$ with respect to the system axis because the adaptation of the image planes of the segment to the spiral path of the respective sub-segment is then better again.

In an embodiment of the invention, the neighboring sub-segments overlap, so the output data belonging to the overlap regions are respectively weighted such that the weights of output data corresponding to one another in the overlapping sub-segments produce a value of one.

The advantage of overlapping sub-segments is that artifacts that would otherwise occur at the adjoining edges of the sub-segments are avoided.

In an embodiment, segment images for a number $n_{ima}$ of inclined image planes are reconstructed for each sub-segment, whereby the image planes have different z-positions $z_{ima}$. Due to the reconstruction of a number of segment images having differently inclined image plane for different z-positions, it is possible—by a suitable selection of the inclination angle γ and of the tilt angle Δ—to optimally adapt the image plane of the respective segment image for each of these z-positions to the sub-segment and to thus utilize the detector array as well as the dose completely in theoretical terms and to the greatest extent in practice. In a preferred embodiment of the invention, the number of inclined image planes intersect in a straight line that proceeds tangentially relative to the sub-segment.

In order to obtain an optimally complete detector utilization and dose utilization, the following applies according to a version of the invention for the extreme values $+\delta_{max}$ and $-\delta_{max}$ of the tilt angle δ of the inclined image planes belonging to a sub-segment:

$$\pm\delta_{max} = \arctan\left(\frac{\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $\gamma_0$ is the value of the inclination angle γ determined for the tilt angle δ=0 according to $$\gamma_0 = \tan\left(\frac{-Sp\alpha}{2\pi R_f \sin\alpha}\right)$$

and b is the width of a detector line and S is the length of the spiral path.

For a high image quality, in another version of the invention the optimum value $\gamma_{min}$ of the inclination angle belonging to a given amount $|\delta_{max}|$ of the maximum value of the tilt angle δ is determined such that an error criterion is met, for example minimum average of the squares of the respective spacings of all points of the sub-segment from the image plane measured in the z-direction, is met.

If the rotational axis, around which the focus rotates around the system axis, is not identical with the system axis but intersects the system axis at an angle referred to as a gantry angle ρ, then the following applies to the inclination angle γ' to be selected:

$$\gamma' = \arctan\frac{Sp\cdot\cos\rho}{\sqrt{4\pi^2\cdot R_f + S^2P^2 + 4\pi\cdot R_f\cos\alpha\sin\rho\cdot Sp}}$$

Here, as well, there is the possibility of determining the appertaining optimum value of the inclination angle γ' for a given magnitude of the maximum value of the tilt angle $|\delta_{max}|$ such that an error criterion, for example minimum average of the squares of the respective spacings of all points of the sub-segment from the image plane measured in the z-direction.

In order to obtain an optimally complete detector and dose utilization, the following is also valid according to a version of the invention for the number $n_{ima}$ of the inclined image planes, for which segment images with inclined plane are generated for each sub-segment:

$$n_{ima} = \text{floor}\left[\frac{sM}{p}\right]$$

wherein s is the length of the sub-segments.

Likewise for an optimally complete detector and dose utilization, the tilt angles δ of the inclined image planes are determined in a version of the invention according to $$\delta(i) = \delta_{max}\frac{2i - (n_{ima} - 1)}{n_{ima} - 1}$$

given the condition of detector lines of equal width.

In order to create the conditions for obtaining transverse tomograms to which the users of CT apparatus are accustomed, a reformatting is provided according to one version of the invention, i.e. a sub-image is generated in a further method wherein a number of segment images are combined. In an embodiment of the invention, it may occur that a number of segment images are combined to form a sub-image by interpolation or by, in particular, weighted averaging.

The reconstruction slice thickness of the sub-images, and thus of the resulting CT image is set according to a preferred embodiment of the invention by weighting the segment images according to the desired reconstruction slice thickness of the sub-image in the combining to form a sub-image.

In a version of the invention the compression is reversed during the course of the combining of the segment images belonging to a sub-segment to form a sub-image exhibiting a uniform pixel matrix. Compared to reversing the compression only during the course of the combining of the sub-images to form the resulting CT image, this offers the advantage of an enhanced image quality. In view of this advantage, compared whereto the somewhat larger quantity of data due to the employment of uncompressed sub-images is negligible.

According to versions of the invention, the pixels of the uniform pixel matrix of a sub-image are acquired by interpolation or by averaging from the pixels of the non-uniform pixel matrix of the segment images when combining the segment images belonging to a sub-segment to form a sub-image.

The above object also is achieved in a computed tomography apparatus operating according to the inventive CT method described above. The comments and discussion above relating to the inventive CT method apply equally to the inventive CT apparatus.

DESCRIPTION OF THE PREFERRED EMBODIMENTS

Figure 1:
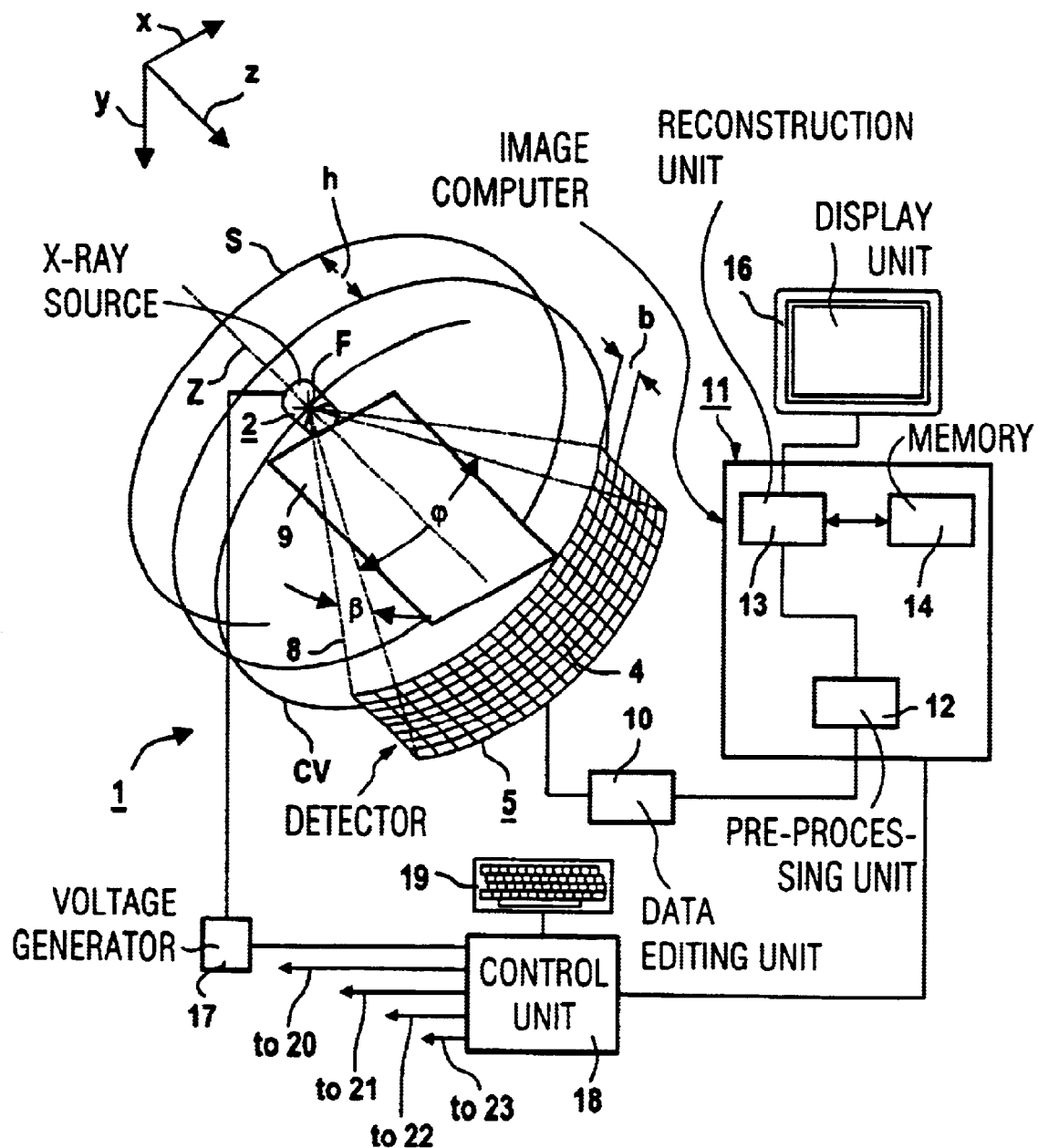
FIG. 1 is a perspective view, with a block circuit diagram presentation of a CT apparatus having multiple lines of detector elements constructed and operating in accordance with the invention.
Figure 2:
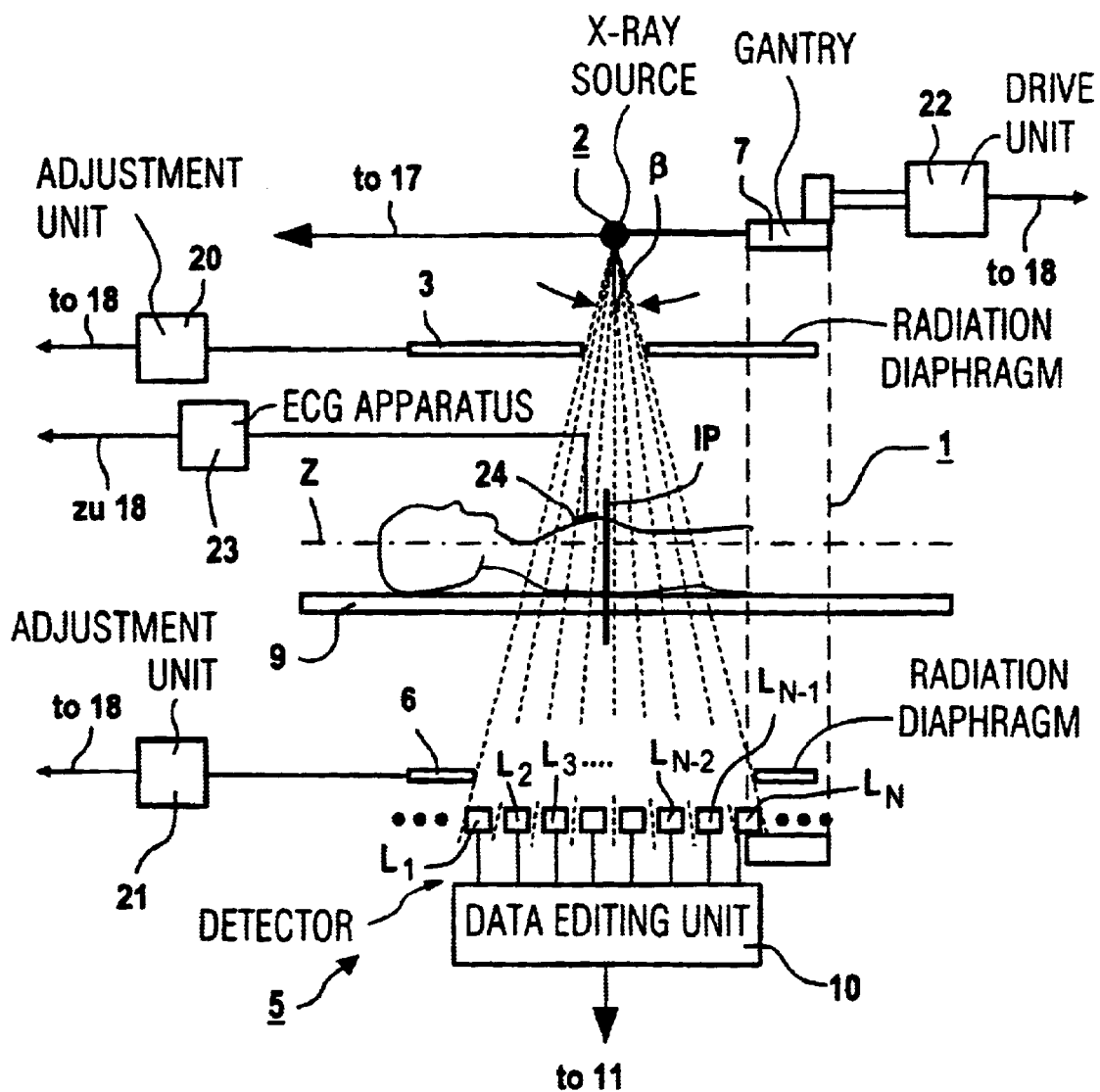
FIG. 2 is a longitudinal section through the apparatus of FIG. 1 in a first operating mode.

FIGS. 1 and 2 show a CT apparatus of the third generation suitable for the implementation of the inventive method. The measurement arrangement 1 thereof has an x-ray source 2 with a source-proximate radiation diaphragm 3 (FIG. 2) preceding it and a detector system 5 fashioned as a planar array of a number of rows and columns of detector elements, one of which is referenced 4 in FIG. 1. The detector system 5 has a detector-proximate radiation diaphragm 6 (FIG. 2) preceding it. For clarity, only eight lines of detector elements 4 are shown in FIG. 1; as indicated dot-dashed in FIG. 2, however, the detector system 5 has (or can have) more lines of detector elements.

Figure 3:
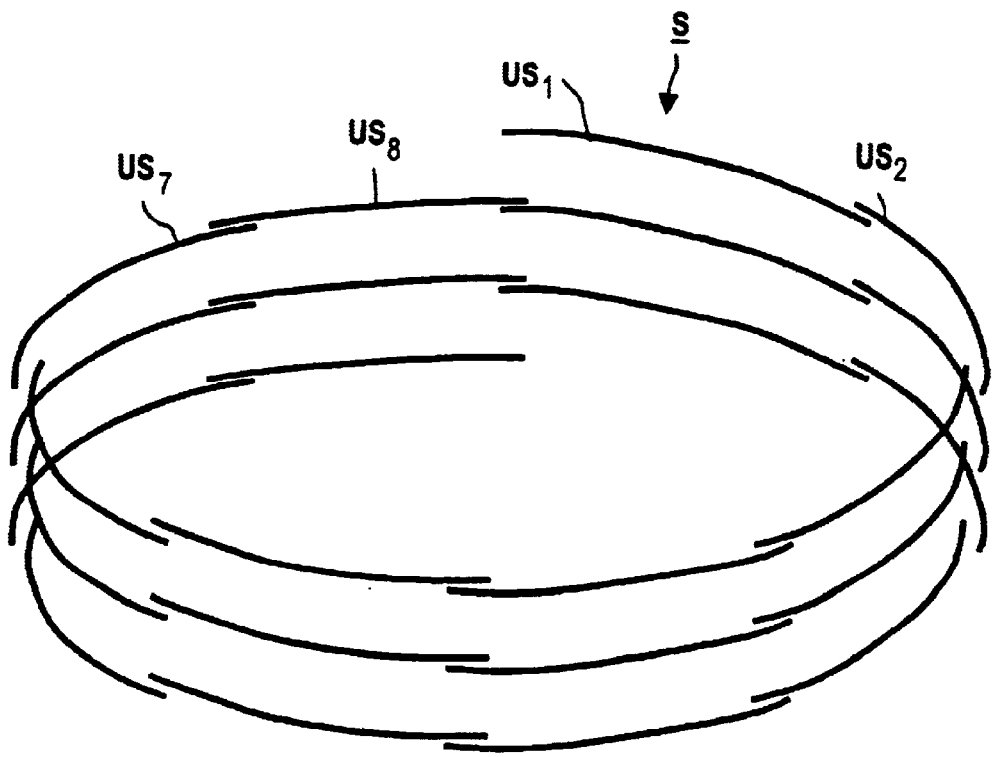
FIG. 3 illustrates the spiral path described by the focus of the x-rays in a spiral scan in the CT apparatus according to FIGS. 1 and 2.

The x-ray source 2 with the radiation diaphragm 3, and the detector system 5 with the radiation diaphragm 6, are opposite one another on a rotary frame 7 as shown in FIG. 3 such that a pyramidal x-ray beam (whose edge rays are referenced 8), that emanates from the x-ray source 2 during operation of the CT apparatus and is gated by the adjustable radiation diaphragm 3, strikes the detector system 5. The radiation diaphragm 6 is set corresponding to the cross-section of the x-ray beam that is set with the radiation diaphragm 3 so that only that region of the detector system 5 is activated that can be directly struck by the x-ray beam. In the operating mode shown in FIGS. 1 and 2, these enabled or activated lines are eight lines of detector elements 4, which are referred to as active lines below. The further lines indicated by dots are covered by the radiation diaphragm 6 and therefore are not active. Each line of detector elements 4 has a K detector element, respectively designated by a channel index k=1 through K. The active lines $L_n$ of detector elements 4 are referenced in FIG. 2 as $L_1$, through $L_N$, respectively indicated by a line index n=1 through N.

The x-ray beam exhibits the cone angle $\beta$ shown in FIG. 2 which is the aperture angle of the x-ray beam in a plane containing the system axis Z and the focus F. The fan angle $\phi$ of the x-ray beam also is shown in FIGS. 1 and 2, this being the aperture angle of the x-ray beam in a plane that is oriented at a right angle relative to the system axis Z and containing the focus F.

The rotary frame 7 can be placed into rotation around the system axis Z by a drive 22. The system axis Z proceeds parallel to the z-axis of a spatial rectangular coordinate system shown in FIG. 1.

The columns of the detector system 5 likewise proceed in the direction of the z-axis, whereby the lines (rows), whose width W is measured in the direction of the z-axis and amounts, for example, to 1 mm, proceeding transversely relative to the system axis Z and the z-axis.

In order to be able to introduce an examination subject, for example a patient, into the beam path of the x-ray beam, a support mechanism 9 is displaceable parallel to the system axis Z, i.e. in the direction of the z-axis, with a synchronization between the rotational motion of the rotary frame 7 and the translational motion of the support mechanism 9 that causes the ratio of translational to rotational velocity to be constant. This ratio can be set by selecting a value for the feed h of the support mechanism 9 per revolution of the rotary frame 7.

A volume of an examination object situated on the support mechanism 9 thus can be examined during the course of a volume scan. The volume scan can be undertaken in the form of a spiral scan in the sense that, given simultaneous rotation of the measurement unit 1 and translation of the support mechanism 9, a number of projections from different projection directions is registered with the measurement unit per revolution of the measurement unit 1. In the spiral scan, the focus F of the x-ray source moves on a spiral path (referenced S in FIG. 1) relative to the support mechanism 9.

The measured data corresponding to the individual projections and read out in parallel during the spiral scan from the detector elements of every active line of the detector system 5 are subjected to a digital-to-analog conversion in a data editing unit 10, and are serialized and transmitted to an image computer 11.

After a pre-processing of the measured data in a pre-processing unit 12 of the image computer 11, the resulting data stream proceeds to a reconstruction unit 13 that reconstructs CT images of desired slices of the examination subject from the measured data, either according to methods that are known themselves (for example, 180 LI or 360 LI interpolation) or, in an operating mode corresponding to the invention, according to a method that is explained in greater detail.

The CT images are composed of pixels arranged in a matrix, with the pixels being allocated to the respective image plane. A CT number in Hounsfield units (HU) is allocated to each pixel, and the individual pixels, corresponding to a CT number/gray scale value—are presented in a gray value corresponding to the respective CT number.

The images reconstructed by the tomogram reconstruction unit 13 and the x-ray shadowgram reconstruction unit are displayed at a display unit 16, for example a monitor, connected to the image computer 11.

The x-ray source 2, for example an x-ray tube, is supplied with the necessary voltages and currents, for example the tube current U, by a generator unit 17. In order to be able to set these parameters to the necessary values, the generator unit 17 has a control unit 18 with a keyboard 19 which allows the necessary settings.

The rest of the operation and control of the CT apparatus ensues with the control unit 18 and the keyboard 19, this being illustrated by the connection of the control unit to the image computer 11.

Among other things, the number N of active lines of detector elements 4, and thus the position of the radiation diaphragms 3 and 6, can be set, for which purpose the control unit 18 is connected to adjustment units 20 and 21 allocated to the radiation diaphragms 3 and 6. Further, the rotation time $\tau$ can be set, which is time the rotary frame 7 requires for a complete revolution. This is illustrated by the connection of the drive unit 22 for the rotary frame 7 to the control unit 18.

An ECG device 23 is provided in order to additionally allow examination of a region of the patient P that executes a periodic motion, namely the patient's heart. One of the electrodes connected to the ECG device 23 is shown in FIG. 2 and referenced 24. The signal generated by the ECG device 23 is supplied to the computer 18, which stores this during the implementation of an examination, i.e. a spiral scan of the patient P.

To that end, a spiral scan is implemented over a length that suffices at least for the reconstruction of a CT image. In the example illustrated in FIG. 3, this is a spiral scan of the length 6π. Measured data corresponding to a number of overlapping sub-segments are obtained from the measured data thereby acquired, with the length of each sub-segment being less than the length required for the reconstruction of a CT image. The number and length, for example π/4 or π/8, of the sub-segments are selected such that they produce at least one spiral segment overall having length, for example π+φ, that suffices for the reconstruction of a CT image, i.e. it is at least equal to the length required for the reconstruction of a CT image. A number of $N_{tilt}$ of segment images, whose pixels relate to different image planes inclined relative to the middle plane, is calculated for each of the sub-segments from the corresponding measured data.

It can be seen from FIG. 3 that 8 overlapping sub-segments are present per full revolution in the described exemplary embodiment, i.e. $N_\alpha$=8. The sub-segments of the first of the three full revolutions shown in FIG. 3 are referenced $US_1$ through $US_{12}$ in FIG. 3.

Figure 4:
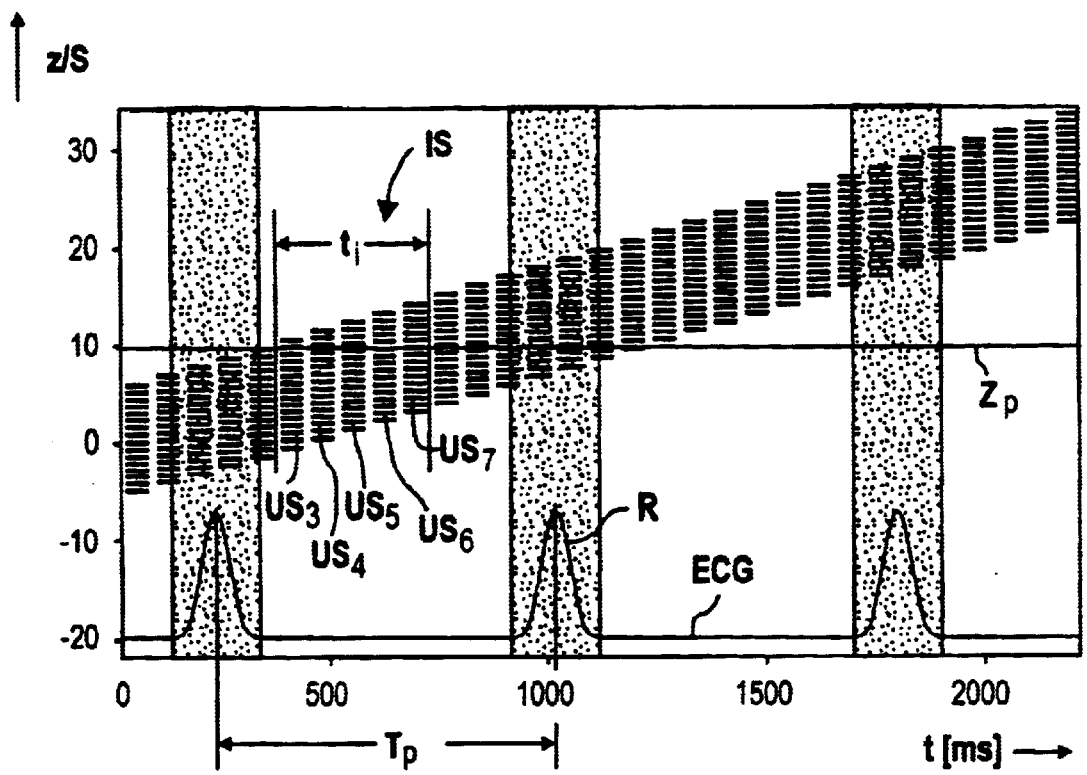
FIG. 4 is a diagram illustrating the data registration ensuing according to a first operating mode together with the registration of an ECG in accordance with the invention.

In the case of, for example, sixteen active lines of detector elements 4, sub-segments are thus obtained in the way illustrated in FIG. 4 that exhibit a time position with respect to the ECG signal that is likewise schematically indicated in FIG. 4 and referenced ECG. Moreover, these data packets—that corresponding to the sub-segment $US_4$ is referenced $US_4$ as an example—exhibit a z-position corresponding to the spiral path S described by the focus F dependent on the sub-segment to which they belong.

When a resulting CT image is to be calculated for a specific z-position, which is indicated by a broken line $z_p$ in FIG. 4, the data in the time windows with the gray underlay that are acquired in the region of the R-wave of the ECG (referenced R) are normally omitted, since movements of the heart are present in the region of the R-waves that are too pronounced in order to enable a reconstruction of a sharp image. Given the pre-condition of an adequately short rotation time T, however, the data registered in the region of the R-wave can also be utilized.

It is particularly the data that are acquired between the first and second R-waves in FIG. 4 that are suitable in view of the desired Z-position of the resulting CT image. This is because such data cover a region referenced I in FIG. 1 that corresponds to a spiral segment whose length corresponds to five sub-segments ($N_{\alpha r}$=5) and thus suffices for the reconstruction of a resulting CT image, and because a phase of relatively slight heart activity, i.e. motion, respectively lies between two R-waves.

In a first operating mode of the exemplary embodiment, five segment images are calculated per sub-segment, as can be seen from FIG. 4 with reference to the example of the sub-segment $US_4$, i.e. $N_{tilt}$=5, this being illustrated by the image planes $PI_1$ through $PI_5$ of the segment images.

For a full revolution, thus, a total of $N_\alpha * N_{tilt}$=60 segment images are calculated from the measured data of the full revolution, with the segment images belonging to a sub-segment being combined later to form a sub-image.

The image planes $PI_1$ through $PI_5$ of the segment images all intersect in a straight line according to FIG. 4. In the illustrated exemplary embodiment, this line is the tangent T at the middle M of the sub-segment in question, i.e. that point of the portion of the focal path belonging to the sub-segment that lies at half the arc length of this portion of the focal path.

Those measured values that correspond to the line integrals required for a reconstruction of the respective segment image are selected for each of these image planes $PI_1$ through $PI_5$ from the measured data that are supplied by the various detector lines $L_1$ through $L_8$. The selection ensues such that the beams utilized for reconstruction of the respective segment image satisfy a suitable error criterion with respect to their distance from the inclined image plane of the respective segment image. In the exemplary embodiment, this is the minimum average of the squares of the distances measured in the z-direction, of all rays utilized for the reconstruction of the respective segment image, from the respective, inclined image plane $PI_1$ through $PI_5$.

The maximum inclination of an image plane of a segment image thus is defined by the requirement that measured values must be available for all required line integrals whose rays lie adequately close to the inclined image plane according to the error criterion.

The segment image belonging to each image plane $PI_1$ through $PI_5$ is then calculated from these line integrals compiled for each image plane $PI_1$ through $PI_5$ from different measured values, for example by means of the standard reconstruction method of convolution and back-projection. The pixels of these segment images belong to the respective, inclined image plane $PI_1$ through $PI_5$. In the described exemplary embodiment, thus, a stack of five segment images is calculated for each sub-segment.

The $N_{tilt}$ segment images obtained in this way per sub-segment are combined in a following reformatting step to form a sub-image with respect to a desired target image plane IP that is different from the image planes $PI_1$ through $PI_5$ and intersects the system axis Z, preferably at a right angle as shown in FIG. 2, dependent on selectable combining modes (explained below) either by weighting or by interpolation. Independently of the combining mode, the image noise is reduced during the course of the combining, and the desired reconstruction slice thickness is set, with the setting of the segment images ensuing by means of the weighting and/or the number of the segment images involved in the reformatting. This number preferably equals to the number of segment images reconstructed per sub-segment.

The $N_\alpha$ sub-images obtained in this way are combined with respect to the target image plane to form a resulting CT image in a final reformatting step, by addition.

The combining of segment images to form a sub-image ensues in a first combining mode by weighting, by either of two selectable weighting modes. Independently of the selected weighting mode, the pixels of the segment images respectively contribute as source pixels to a corresponding target pixel of the resulting CT image, and the magnitude of a source pixel relative to a target pixel is weighted dependent on a geometric reference quantity. In other words: the CT number belonging to a target pixel is determined from the CT numbers of the corresponding source pixels taking the geometrical reference quantity into consideration.

In the first weighting mode, the distance of the respective source pixel from the corresponding target pixel is taken into consideration as the geometrical reference quantity.

In the second weighting mode, a weighting dependent on the distance of the source pixel from the middle of the sub-segment in question additionally ensues in order to avoid artifacts.

In a second combining mode, the combining of the segment images to from a sub-image ensues by interpolation, i.e. the target pixels—the pixels of the resulting CT image—are determined by interpolation, for example linear interpolation, from the corresponding source pixels, i.e. from the corresponding pixels of the segment images.

The conditions underlying the reconstruction of segment images shall be explained as an example below on the basis of a sub-segment that is centered with respect to a reference projection angle $\alpha_r=0$. Since the image planes of the $n_{ima}$ segment images are inclined relative to the x-axis by the inclination angle $\gamma$ as well as relative to the y-axis by the tilt angle $\delta$, a normal vector of an image plane is established by:

$$\vec{n}(\gamma, \delta) = \begin{pmatrix} \sin\delta \\ -\cos\delta\sin\gamma \\ \cos\delta\cos\gamma \end{pmatrix} \quad (1)$$

The distance $d(\alpha, \delta, \gamma)$ that an arbitrary point $(x_f, y_f, z_f)$ on the spiral path, or the sub-segment under consideration, has from the image plane inclined by the inclination angle $\gamma$ and the tilt angle $\delta$ is established by $$d(\alpha, \delta, \gamma) = \vec{n}(\gamma, \delta) \cdot \begin{pmatrix} x_f + R_f \\ y_f \\ z_f \end{pmatrix} = \vec{n}(\gamma, \delta) \cdot \begin{pmatrix} -R_f\cos\alpha + R_f \\ -R_f\sin\alpha \\ Sp\frac{\alpha}{2\pi} \end{pmatrix} \quad (2)$$

$$= R_f(1-\cos\alpha)\sin\delta + R_f\sin\alpha\cos\delta\sin\gamma + Sp\frac{\alpha}{2\pi}\cos\delta\cos\gamma$$

It is assumed that the position $(-R_f, 0, 0)$ of the focus F lies in the image planes for the reference projection angle $\alpha_r=0$. The inclination angle $\gamma$ and the tilt angle $\delta$ of the inclined image plane must be selected such that all points of the sub-segment in question satisfy an error criterion, for example that the average of the squares of the distances in the z-direction of all points of the spiral segment from the image plane is minimized.

When it is assumed that b–t is the coordinate system x–y rotated by an angle $\alpha-\pi/2$ around the z-axis, then b–t is the local coordinate system for a projection having the projection angle $\alpha$.

$$x = b\sin\alpha + t\cos\alpha$$

$$y = -b\cos\alpha + t\sin\alpha \quad (3)$$

When a virtual detector array is imaged that corresponds to the projection of the detector array into a plane containing the system axis z, referred to as the virtual detector plane, then t=0 applies to the detector plane.

Each point (x,y,z) on the image plane is characterized by $$\vec{n}(\gamma, \delta) \cdot \begin{pmatrix} x + R_f \\ y \\ z \end{pmatrix} = (x+R_f)\sin\delta - y\cos\delta\sin\gamma + z\cos\delta\cos\gamma = 0 \quad (4)$$

When (3) with t=0 is introduced into (4), then the intersecting straight line of the virtual detector plane with the image plane is obtained:

$$z(b) = -R_f\frac{\tan\delta}{\cos\gamma} - b\left(\sin\alpha\frac{\tan\delta}{\cos\gamma} + \cos\alpha\tan\gamma\right) \quad (5)$$

The z-coordinate on the virtual detector plane is established by $$z_{Det}(b) = z(b) - Sp\frac{\alpha}{2\pi} = -R_f\frac{\tan\delta}{\cos\gamma} - Sp\frac{\alpha}{2\pi} - b\left(\sin\alpha\frac{\tan\delta}{\cos\gamma} + \cos\alpha\tan\gamma\right) \quad (6)$$

The inclination angle $\gamma$ is first optimized in the same way as in the case of U.S. Pat. No. 5,801,134, i.e. for the tilt angle $\delta=0$. The following is obtained as a result:

$$\tan\gamma_0 = \frac{-Sp\bar{\alpha}}{2\pi R_f \sin\bar{\alpha}}, \quad (7)$$

wherein $\bar{\alpha}$ is the angle at which the sub-segment penetrates the image plane.

The tile angle $\delta$ is optimized for the tilt angle $\gamma_0$ obtained with $\bar{\alpha}$ according to (7). The optimization criterion for the tilt angle $\delta$ is that the z-coordinate according to (6) for the detector lines $-RFOV \leq b \leq RFOV$ that limit the region of the examination subject acquired by the radiation toward the back or front in the z-direction must lie within the active detector area, i.e. within the region of the detector array 5 enabled by the radiation diaphragm 6 and struck by the radiation, also must utilize the detector area optimally well.

For the maximally possible tilt angle $\pm\delta_{max}$, the lines for $b=\pm RFOV$ established by the z-coordinate according to (6) reach the front or back end of the detector surface in the z-direction. When this occurs for the respective sub-segment for the projections at the start and end of the sub-segment, i.e. for the outermost projection angle $\pm\alpha_1$, the following applies:

$$z_{Det}(b = \pm RFOV) = \pm\frac{bM}{2}. \quad (8)$$

wherein M is the number of detector lines and W is the width of a detector line measured in the z-direction.

By introducing (5) for $\alpha=\alpha_1$ and $\gamma=\gamma_0$ into (7) and solving for $\delta_{max}$, the following results:

$$\tan\delta_{max} = \frac{\frac{bM}{2} + Sp\frac{\alpha}{2\pi} \pm RFOV\cos\alpha_1\tan\gamma_0}{-\frac{R_f}{\cos\gamma_0} - (\pm RFOV)\frac{\sin\alpha_1}{\cos\gamma_0}} \quad (9)$$

or $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

A new $\gamma_{min}$ is determined for the corresponding $\delta_{max}$ by iteration, namely by minimizing the average of the squares of the distances $d(\alpha, \delta_{max}, \gamma)$ in the z-direction of all points of the sub-segment from the image plane according to (2).

The range $[-\delta_{max}, \delta_{max}]$ of the tilt angle that is available is now uniformly subdivided according to the number $n_{ima}$ of the segment images to be reconstructed, preferably as in the case of the described exemplary embodiment. This means that given a uniform subdivision, each image plane $0 \leq i \leq n_{ima}-1$ is characterized by the inclination angle $\gamma_{min}$ (that, as in the case of the described exemplary embodiment, is preferably the same for all image planes) and by the respective tilt angle $\delta_{(i)}$, with the following being applicable for the respective tilt angle:

$$\delta(i) = \delta_{max} \frac{2i - (n_{ima} - 1)}{n_{ima} - 1} \quad (10)$$

The number $n_{ima}$ of the segment images to be reconstructed for the sub-segment is established by $$n_{ima} = \text{floor}\left[\frac{sM}{p}\right]. \quad (11)$$

wherein s is the arc length of the spiral path S for the sub-segment under consideration.

The reformatting occurs using interpolation functions of a selectable width, as a result of which the slice sensitivity profile and the image noise in the resulting transverse tomogram can be influenced.

It is advantageous that the definition of the desired reconstruction slice thickness of the sub-images, and thus of the resulting CT images, ensues retrospectively during the course of the reformatting.

The plurality of segment images required in the reformatting to be implemented for the acquisition of a sub-images is obtained in the following way:

At the edge of the object cylinder parameterized by $(x,y)=(R_M \cos(\phi), R_M \sin(\phi))$, the distance $\Delta z_R$ of an image plane inclined by the inclination angle and the tile angle with the normal vector $$\vec{n}(\gamma, \delta) = \begin{pmatrix} \sin\delta \\ -\cos\delta\sin\gamma \\ \cos\delta\cos\gamma \end{pmatrix}$$

and with the zero point in the point $(-R_f, 0, z_r)$, is obtained by inserting $(x,y,\Delta z_R)$ is inserted into the plane equation $\vec{n}(\delta,\gamma) \cdot \vec{x} = 0$.

The following then results:

$$\Delta z_R = -\frac{\tan(\delta)}{\cos(\gamma)} \cdot (-R_f + R_M \cdot \cos(\Phi)) + \tan(\gamma) \cdot R_M \cdot \sin(\Phi). \quad (12)$$

For the reformatting of a transverse tomogram with the image plane in $z_R$, accordingly, all segment images reconstructed in the interval $$[((z_R - sup_\Phi \cdot \Delta z_R(\Phi,\delta))),((z_R + sup_\Phi \Delta z_R(\Phi,\delta)))] \quad (13)$$

must be available, i.e. must be stored in the memory 14.

When an interpolation function whose length z* exceeds the limits placed by the above interval is employed in the reformatting, then the number of segment images required for the reformatting is defined by the length of the interpolation filter.

In the general case, the following is valid for the number $N_M$ of the reconstructed images with inclined image plane required for the reformatting of a sub-image:

$$N_M = 2 \cdot \max(z^*, sup_\Phi \Delta z_R) / W \cdot N_S \quad (14)$$

$N_S$ is the number of segment images reconstructed per width W of a line of detector elements.

In the above-described operating mode, the resulting CT images are generated in an indirect way from segment images by combining segment images belonging to a sub-segment to form a sub-image and the sub-images are combined to form the resulting CT image. All sub-images to be reconstructed according to Equation (14) for the sub-segments lying in the selected interval I are reconstructed and taken into consideration in the combining into sub-images and thus in the resulting CT image. In a version of this mode, only a portion of the segment images belonging to a sub-segment is selected, for example taking the z-position of the respective plane into consideration, and is involved in the combining into sub-images, and thus into a resulting CT images.

In a further operating mode, the resulting CT image is acquired directly, i.e. without the detour via sub-images, from the segment images belonging to the region I that are again preferably selected on the basis of their z-position. Only one segment is reconstructed per sub-segment, namely a segment image that corresponds to the target image plane in view of its z-position or lies optimally close to the target image plane. Insofar as the z-position of a selected segment image does not correspond to the target image plane, a reformatting of the segment image onto the target image plane ensues, for example by weighting dependent on the distance of the pixels of the segment image from the target image plane.

Figure 8:
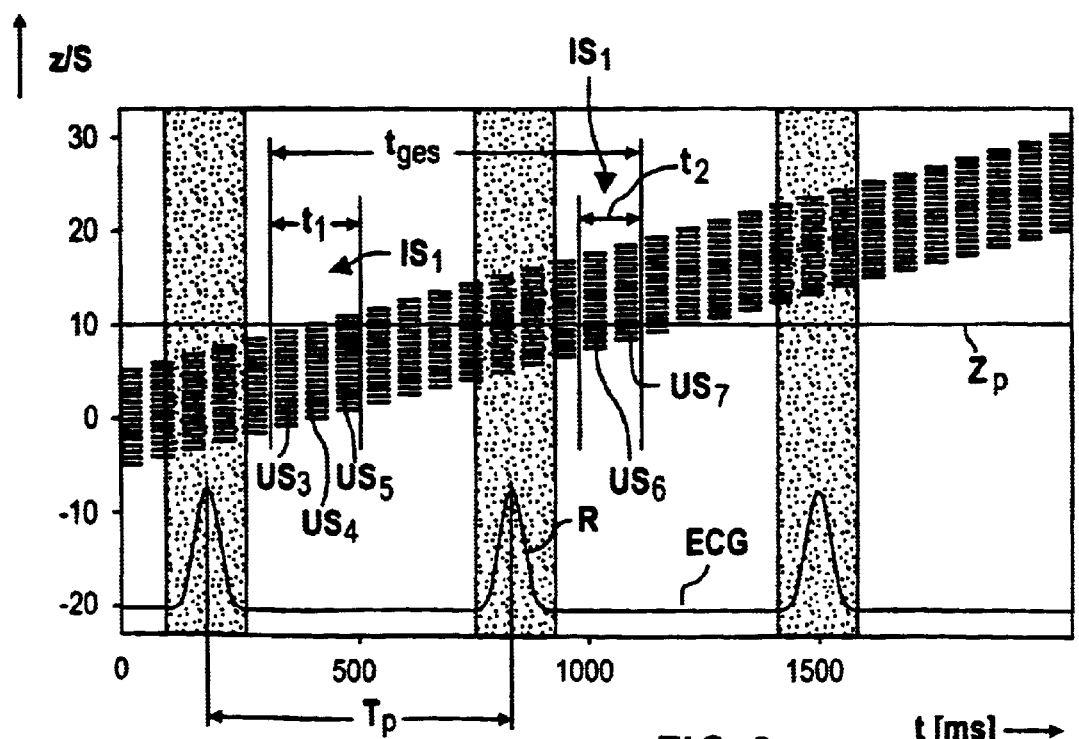
FIG. 8 shows another operating mode in accordance with the invention in an illustration analogous to FIG. 4.

In an alternative operating mode illustrated in FIG. 8 and in contrast to the operating mode according to FIG. 4, the segment images to be selected for the reconstruction of a resulting CT image are not taken from one phase, but from a number of phases of the periodic motion of the heart. The images are taken from two successive phases in the case of the exemplary embodiment shown in FIG. 8, and from the regions $I_1$ and $I_2$ therein. The time span $t_{ges}$ for the data underlying the resulting CT image is in fact longer than in the case of the operating mode according to FIG. 4, wherein $t_{ges}$ is equal to the duration $t_1$ of the region I. The segment of the heart cycle illustrated in the resulting CT image indicates that the operating mode according to FIG. 8 is shorter than of the operating mode according to FIG. 4 as a result of the fact that the time window corresponding to the region $I_2$ taken from the second period and having the duration $t_2$ and the time window corresponding to the region $I_1$, taken from the first period and having the duration t1 are always shorter then the time window ti in the operating mode according to FIG. 4.

It is thus clear that a higher time resolution with reference to the duration of a heart cycle is achieved in the operating mode according to FIG. 8.

The variations described in conjunction with the operating mode according to FIG. 4 are also applicable in the case of the operating mode according to FIG. 8.

In the operating mode according to FIG. 4 as well as according to FIG. 8, resulting CT images for further z-positions are obtained in a volume operating mode in the way described for the z-position $z_p$. These further z-positions are selected such that the slices shown in the corresponding, resulting CT images preferably directly adjoin one another and the resulting CT images are calculated until volume data with respect to a desired volume are present, such that the time position is the same for the various CT images.

In the volume operating mode, segment images are expediently reconstructed for all quiescent phases covered in the scanning and lying between successive R-waves in order to assure that all required segment images are in fact available in the acquisition of the volume data.

In all described operating modes, the slope of the spiral path must be limited in the way known, for example, from German OS 198 42 238 such that the sub-volumes for a spiral segment having an overall length adequate for the reconstruction of a CT image fit to one another without gaps in the z-direction, i.e. in the direction of the system axis.

Figure 9:
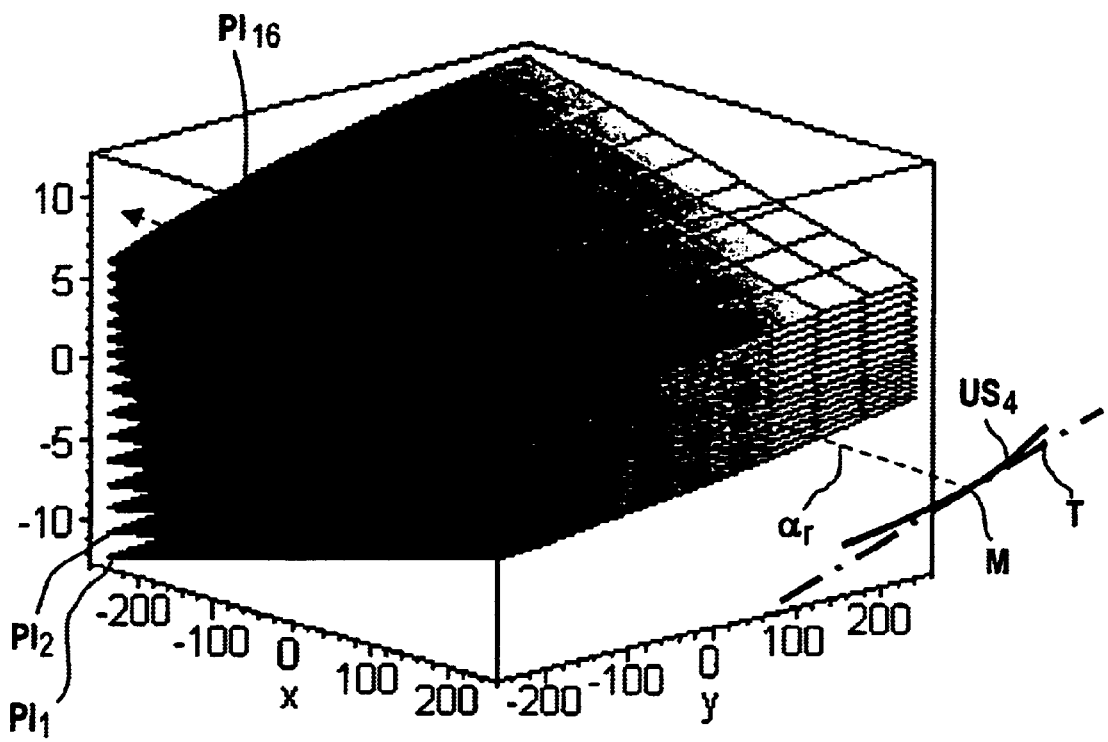
FIG. 9, in an illustration analogous to FIG. 5, shows the image areas of the segment images belonging to a sub-segment, these image areas being curved according to this version of the invention.
Figure 10:
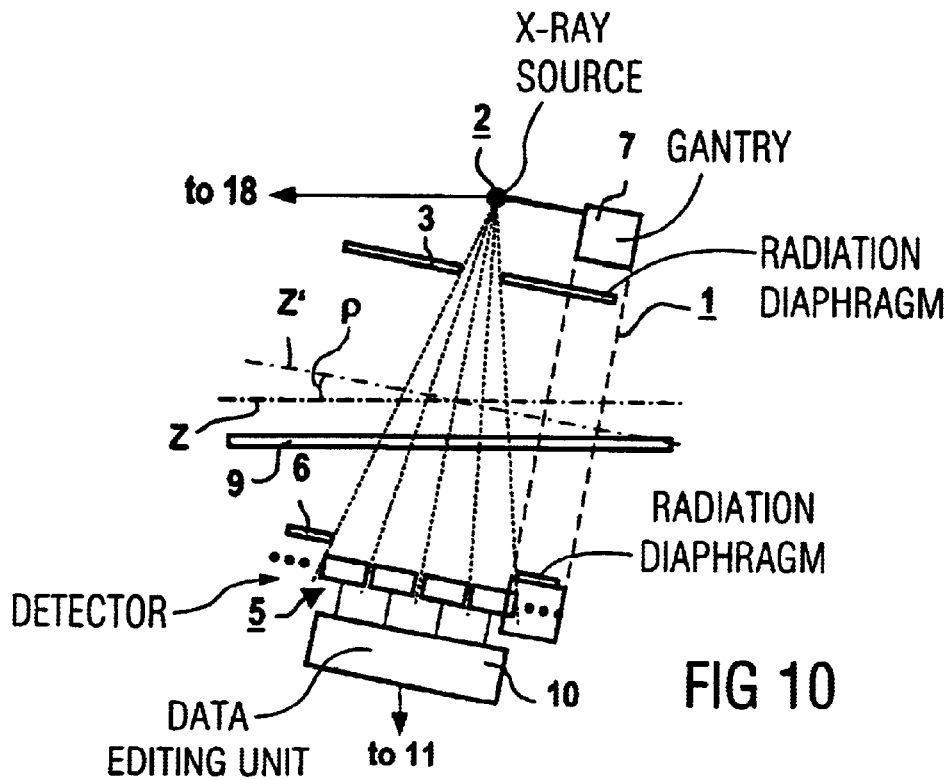
FIG. 10 shows another operating mode of the CT apparatus according to FIGS. 1 and 2, in an illustration analogous to FIG. 2.

So that the feed h is not unnecessarily limited, an operating mode can be selected wherein, departing from the above mode, the image planes of the segment images are not flat but are curved as shown in FIG. 9. Sixteen image planes $PI_1$ through $PI_{16}$ are provided in this case. As set forth above for planar image surfaces, it is also assured on the basis of an error criterion in the case of curved image planes that a good adaptation is established.

As a result of the fact that the reconstruction slice thickness of a desired sub-tomogram is retrospectively defined, the reconstruction of the segment images preferably ensues by selecting a correspondingly narrow weighting function with the least possible reconstruction slice thickness. This assures utmost sharpness in the z-direction not only of the segment images but also of the sub-images obtained by the reformatting as well as of the CT image acquired therefrom.

In addition to this advantage, the following are further advantages of the described reformatting:

The reconstruction slice thickness can be retrospectively selected without a renewed reconstruction being required;

The reconstruction slice thickness is freely selectable; and

A number of suitable interpolation functions having a freely selectable width is available for the reformatting.

Figure 6:
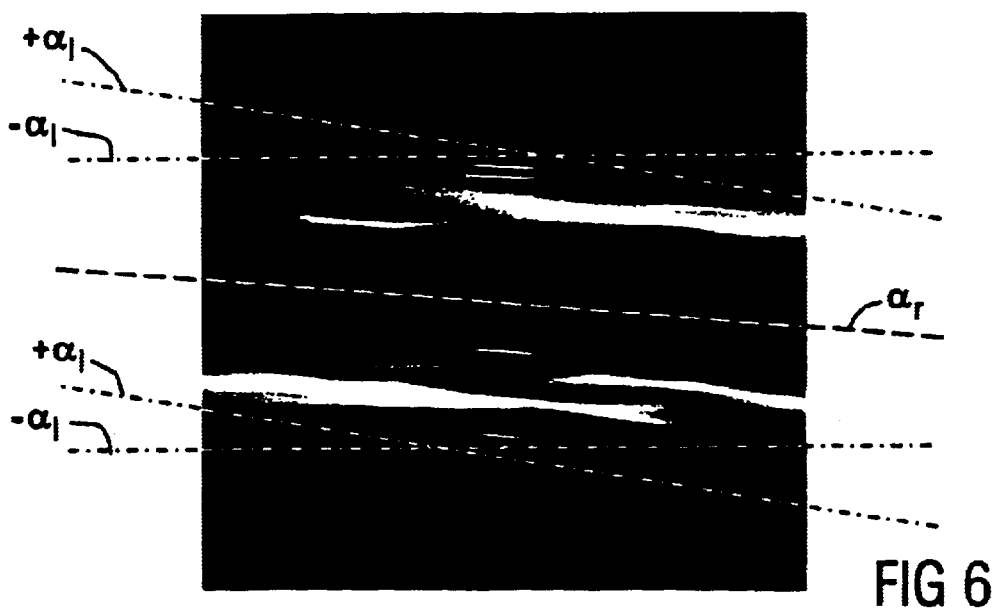
FIG. 6 illustrates an example of a segment image in accordance with the invention.

FIG. 6 illustrates the segment image belonging to the image plane $PI_3$ as an of example from among the segment images belonging to the sub-segment $US_4$. The reference projection angle $\alpha_r$ and the outermost projection angles $+\alpha_1$ and $-\alpha_1$ belonging thereto are indicated with broken lines. It can be seen that the information density in the segment images that are orthogonal relative to the projection direction corresponding to the respective reference projection angle (referred to below as the reference projection direction) is significantly greater than in the reference projection direction.

There is therefore the possibility of compressing the data corresponding to the segment images. In the described exemplary embodiment and as a result of the fact that the data redundancy would be extremely high for the aforementioned reasons when employing a uniform pixel matrix, the data compression occurs in that the compressed data corresponding to the segment images has such a non-uniform pixel matrix corresponding to the data structure that the resolution $R_r$ in reference projection direction is less then the resolution $R_{or}$ orthogonally relative to the reference projection direction. When a given resolution orthogonally relative to the reference projection direction is assumed, then the compression factor that can be achieved in the compression corresponds to the quotient $R_{or}/R_r$.

Figure 7:
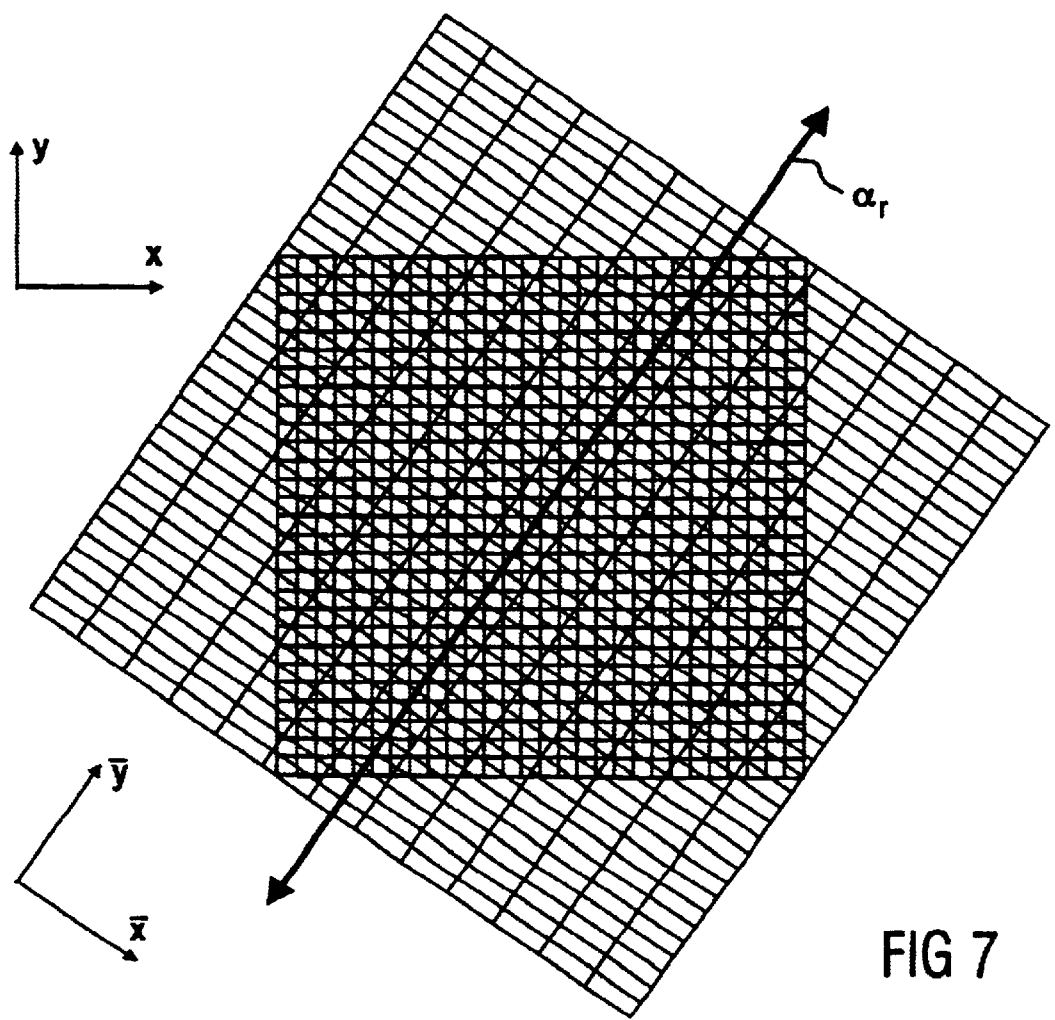
FIG. 7 illustrates the non-uniform pixel matrix of a segment image and the uniform pixel matrix of the appertaining sub-image in accordance with the invention.

In the described exemplary embodiment, the non-uniform pixel matrix is realized according to FIG. 7 wherein it can be seen that the compressed data corresponding to the segment images are represented as pixels having an oblong, shape, such as a rectangular shape, with the longest extent of the pixels proceeding in the reference projection direction.

If it is desired to reduce the memory space required for storing the segment images, a first compression operating mode is selected wherein the segment images are converted into the non-uniform pixel matrix after the reconstruction has ensued.

If it is also desired to reduce the calculating outlay required for the reconstruction of the segment images, a second compression operating mode is selected wherein the segment images are already reconstructed in the non-uniform pixel matrix. This offers the advantage that significantly fewer pixels need to be reconstructed than in the case of a uniform matrix that exhibits the same resolution orthogonally to the reference projection direction as the non-uniform pixel matrix.

Figure 5:
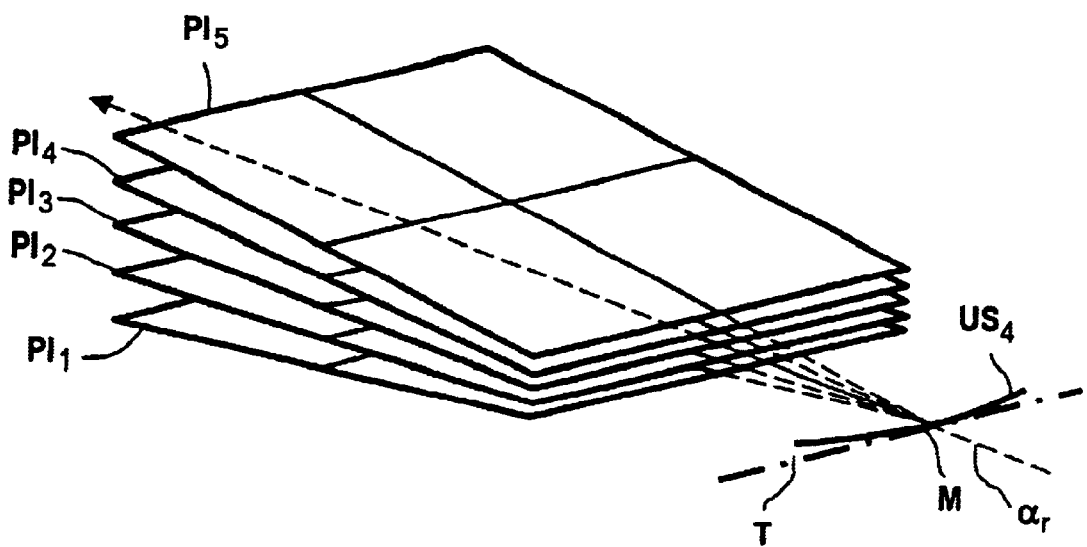
FIG. 5 illustrates the image planes of the segment images belonging to a sub-segment in accordance with the invention.

During the course of the reconstruction in the non-uniform matrix, the coordinate system with the axis and the axis underlying the back-projection is rotated according to FIG. 5 such that the back-projection direction corresponds to the respective reference projection direction.

Regardless of which of the two compression operating modes is selected, the data compression must in turn be canceled no later than during the combining of the sub-images to form a resulting CT image.

To that end, the inventive CT apparatus can be operated in a first decompression operating mode such that the sub-images are also generated on the basis of the non-uniform pixel matrix, and the transition to a uniform pixel matrix only ensues during the course of the generation of the resulting CT image.

In a second decompression operating mode, a switch to the uniform pixel matrix already is made in the combining of the segment images belonging to a sub-segment to form a sub-image. This offers the advantage of an enhanced image quality compared to a decompression that is delayed until the sub-images are combined into the resulting CT image.

Regardless of whether the decompression ensues during the course of the combining of segment images to form a sub-image or the combining of sub-images to form a resulting CT image, the pixels of the uniform pixel matrix, in a selectable first operating mode, are acquired by interpolation from the pixels of the uniform pixel matrix. Given selection of a second operating mode, the pixels of the uniform pixel matrix are acquired from the pixels of the non-uniform pixel matrix by weighting.

As a result of the alignment of the non-uniform pixel matrix corresponding to the reference projection direction, the non-uniform pixel matrix must be larger than the uniform pixel matrix in both of the just-described operating modes in order, despite the rotation of the non-uniform pixel matrix relative to the uniform pixel matrix, to assure that the non-uniform pixel matrix contains data suitable for the determination of each pixel of the uniform pixel matrix. In the case of a quadratic uniform pixel matrix and a likewise quadratic non-uniform pixel matrix, this means that the side length (for arbitrary reference projection directions) of the non-uniform pixel matrix must be greater than that of the uniform pixel matrix.

As to the procedure in the data decompression by means of interpolation or weighting, the discussion above in conjunction with the combining of a number of segment images to form a sub-image applies analogously, i.e. the averaging also can ensue weighted.

In the described exemplary embodiment, the data compression ensues on the basis of the employment of a non-uniform pixel matrix. Alternatively, other compression methods standard in the field of image processing can be applied.

In an operating mode with inclined rotary frame 7 illustrated in FIG. 7, the rotational axis Z' around which the focus F rotates around the system axis Z is not identical with the system axis Z but intersects this at the gantry angle ρ. Then the geometry according to FIG. 2 yields a tilted coordinate system according to FIG. 7 with the z'-axis corresponding to the middle axis of the spiral path S that is tilted relative to the z-axis by the gantry angle ρ, with the y'-axis that is likewise tilted by the gantry angle ρ relative to the y-axis, and with the x-axis retained unmodified.

The following is valid for the spiral path S in this coordinate system:

$$\vec{x}'_f = \begin{pmatrix} -R_f \cos\alpha \\ -R_f \sin\alpha + Sp\dfrac{\alpha \sin\rho}{2\pi} \\ Sp\dfrac{\alpha \cos\rho}{2\pi} \end{pmatrix} \quad (15)$$

The above-described procedure for determining the maximum tilt angle $\delta_{max}$ can be transferred to the case of the tilted gantry, whereby the following is valid instead of Equation (6):

$$z'_{Det}(b) = z'(b) - Sp\dfrac{\alpha \cos\rho}{2\pi} \quad (16)$$

$$= -R_f \dfrac{\tan\delta}{\cos\gamma} - Sp\dfrac{\alpha \cos\alpha}{2\pi} - b\left(\sin\alpha \dfrac{\tan\delta}{\cos\gamma} + \cos\alpha\tan\gamma\right),$$

The following is derived therefrom for b=±RFOV:

$$z'_{Det}(=\pm RFOV) = \pm \dfrac{bM}{2}\sqrt{1 - \left(\dfrac{b}{R_f}\right)^2 + \alpha \sin\dfrac{b}{R_f} Sp\dfrac{\cos\alpha}{2\pi}} \quad (17)$$

The inclination angle γ' in the coordinate system (x,y',z') for the case of the inclined gantry, however, is now to be introduced into the definition equation for the maximum tilt angle $\delta_{max}$, i.e. into Equation (9).

The following is valid for the inclination angle γ' in the case of the inclined gantry:

$$\tan\gamma' = \partial z \dfrac{\partial z'}{\partial s} \quad (18)$$

$$= \dfrac{\partial z'}{\partial \alpha} \cdot \dfrac{\partial \alpha}{\partial s}$$

$$= \dfrac{Sp \cdot \cos\rho}{\sqrt{4\pi^2 \cdot R_f + S^2\rho^2 + 4\pi \cdot R_f \cos\alpha \sin\rho \cdot Sp}}$$

or $$\gamma' = \arctan \dfrac{S\rho \cdot \cos\rho}{\sqrt{4\pi^2 \cdot R_f + S^2\rho^2 + 4\pi \cdot R_f \cos\alpha \sin\rho \cdot Sp}}$$

It has been found that the inclination angle γ' for the case of the tilted gantry is nearly independent of the reference projection angle $\alpha_r$. It was also found with respect to the maximum tilt angle $\delta_{max}$ that this is nearly independent of the reference projection angle $\alpha_r$.

There is also the possibility in the case of the inclined gantry of determining the appertaining optimum value for the inclination value γ' for a given amount of the maximum value of the tilt angle $|\delta_{max}|$ that, for example, is acquired from (9) on the basis of the result acquired according to (18) from the slope of the spiral path S in such a way that an error criterion is met, for example the minimum average of the squares of the distances measured in z-direction of all points of the sub-segment from the image plane.

In the described exemplary embodiment, the relative motion between the measuring unit 1 and the support mechanism 9 is generated by displacing the support mechanism 9. However, there is also the possibility within the framework of the invention of leaving the support mechanism 9 stationary and instead displacing the measuring unit 1. Within the framework of the invention, there is also the possibility of generating the necessary relative motion by displacing both the measuring unit 1 as well as the support mechanism 9.

The conical x-ray beam in the described exemplary embodiment has a rectangular cross-section. In the framework of the invention, however, other cross-sectional geometries are also possible.

A CT apparatus of the third generation was described in conjunction with the above-described exemplary embodiments, i.e. the x-ray source and the detector system are displaced in common around the system axis during the image generation. The invention, however, also can be employed in conjunction with CT apparatuses of the fourth generation wherein only the x-ray source is displaced around the system axis and interacts with a fixed detector ring, insofar as the detector system is a matter of a multi-line array of detector elements.

The inventive method also can be employed with CT apparatuses of the fifth generation, i.e. a CT apparatus wherein the x-radiation emanates from not only one focus but from a number of foci of one or more x-ray sources displaced around the system axis, insofar as the detector system comprises a multi-line array of detector elements.

The CT apparatus employed in conjunction with the above-described exemplary embodiments have a detector system with detector elements arranged in the fashion of an orthogonal matrix. The invention, however, also can be employed in conjunction with CT apparatus having a detector system with detector elements arranged in a planar array or in some other way.

The invention is suitable not only for the examination of the heart but also is suitable for the examination of other periodically moving regions, for example due to the respiratory activity of the patient, with an appropriate sensor for acquiring the periodic motion being provided.

The above-described exemplary embodiments relate to the medical application of the inventive method. The invention, however, also can be employed beyond medicine, for example in baggage inspection or when investigating materials.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for producing a computed tomography (CT) image comprising the steps of:
    (a) scanning a subject, having a region exhibiting a periodic motion, with a conical x-ray beam emanating from a focus and detecting said beam, after attenuation by said subject, with a matrix-like detector array while moving said focus along a spiral path around said subject relative to a system axis, said detector array generating output data dependent on radiation from said x-ray beam that is incident thereon;
    (b) dividing said output data, for a segment of said spiral path having a length adequate for reconstructing a CT image, into a plurality of datasets respectively for a plurality of sub-segments of said segment, each of said sub-segments having a length shorter than said length adequate for reconstructing a CT image;
    (c) for each of said sub-segments, reconstructing a plurality of segment images having a plane inclined relative to said system axis from the dataset for that sub-segment;
    (d) obtaining a signal representing a time curve of said periodic motion during said scanning;
    (e) allocating a z-position on said system axis and a time position with respect to said periodic motion to the respective segment images;

(f) selecting segment images within a range of z-positions and a range of time positions so that the respective sub-segments of the selected segment images comprise a total length adequate for reconstruction of a CT image; and (g) at least indirectly combining the selected segment images to form a resulting CT image with respect to a target image plane.

2. A method as claimed in claim 1 wherein said periodic motion exhibits phases, and step (f) comprises selecting segment images with respective sub-segments arising from a single phase of said periodic motion.

3. A method as claimed in claim 1 wherein said periodic motion exhibits phases, and step (f) comprises selecting segment images with respective sub-segments arising from a plurality of phases of said periodic motion.

4. A method as claimed in claim 1 wherein step (g) comprises directly combining said selected segment images to form said resulting CT image.

5. A method as claimed in claim 4 wherein step (g) comprises directly combining said selected segment images to form said resulting CT image with respect to a target image plane corresponding to the respective z-positions of the selected segment images.

6. A method as claimed in claim 4 wherein said selected segment images have respective z-positions which differ from said target image plane, and comprising the additional step of reformatting said selected segment images into said target image plane before step (g).

7. A method as claimed in claim 1 comprising, for each of said sub-segments, combining the plurality of segment images to form a partial image with respect to said target image plane, and wherein step (g) comprises combining said partial images to form said resulting CT image.

8. A method as claimed in claim 7 comprising employing all segment images for a respective sub-segment to form said partial image.

9. A method as claimed in claim 8 wherein said resulting CT image represents an image of a slice of said subject, and further comprising repeating steps (a) through (g) for successive, adjacent slices of said subject to produce a resulting CT image of a volume of said subject comprising said slices.

10. A method as claimed in claim 9 wherein said successive slices adjoin each other.

11. A method as claimed in claim 7 comprising combining said plurality of segment images to form said partial image by interpolation.

12. A method as claimed in claim 7 comprising combining said plurality of segment images to form said partial image by averaging.

13. A method as claimed in claim 7 comprising combining said plurality of segment images to form said partial image by weighted averaging.

14. A method as claimed in claim 13 comprising weighting said segment images dependent on a desired reconstruction slice thickness of said partial image.

15. A method as claimed in claim 7 comprising selecting a number of said segment images for combining to form said partial image dependent on a desired reconstruction slice thickness of said partial image.

16. A method as claimed in claim 15 comprising reconstructing said segment images with a smallest possible slice thickness.

17. A method as claimed in claim 15 comprising, for each of said sub-segments, selecting said plurality of images to be combined for generating said partial image according to:

$$N_M = 2 \cdot \max(z^*, sup_\Phi, \Delta z_R) b \cdot N_S.$$

18. A method as claimed in claim 7 comprising combining said partial images with respect to a target image plane that intersects said system axis at a right angle.

19. A method as claimed in claim 7 comprising combining said partial images to form said resulting CT image by adding said partial images.

20. A method as claimed in claim 1 comprising reconstructing at least one of said segment images with a curved image plane.

21. A method as claimed in claim 1 wherein step (c) comprises, for each of said sub-segments, reconstructing a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis.

22. A method as claimed in claim 1 wherein step (b) comprises dividing said output data into sub-segments wherein neighboring sub-segments overlap in overlapping regions, and comprising the additional step of weighting the output data in said overlapping regions so that the respective portions of the output data in said overlap regions belonging to the neighboring sub-segments in that overlap region have respective weightings which, in combination, add to one.

23. A method as claimed in claim 1 wherein step (c) comprises, for each of said sub-segments, reconstructing a plurality of segment images inclined relative to said system axis which have different positions along a z-axis of a Cartesian coordinate system.

24. A method as claimed in claim 23 wherein step (c) further comprises, for each of sub-segments, reconstructing a plurality of images respectively in inclined image planes that intersect in a straight line proceeding tangentially relative to that sub-segment, as said plurality of segment images having a plane inclined relative to said system axis.

25. A method as claimed in claim 23 wherein step (c) comprises, for each of said sub-segments, reconstructing a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis, and wherein, in step (c), for each of said sub-segments, the plurality of segment images associated therewith respectively have image planes inclined relative to said system axis limited by extreme values $+\delta_{max}$, and $-\delta_{max}$ of said tilt angle $\delta$, according to $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $$\gamma_0 = \arctan\left(\frac{-Sp\bar{\alpha}}{2\pi R_f \sin\bar{\alpha}}\right).$$

26. A method as claimed in claim 1 wherein step (a) comprises rotating said focus around a rotational axis that coincides with said system axis.

27. A method as claimed in claim 1 wherein step (a) comprises rotating said focus around a rotational axis that intersects said system axis at a gantry angle ρ and wherein, in step (c), for each of said sub-segments, the plurality of segment images have respective inclination angles γ' according to $$\gamma' = \arctan \frac{Sp \cdot \cos\rho}{\sqrt{4\pi^2 \cdot R_f + S^2 p^2 + 4\pi \cdot R_f \cos\alpha \sin\rho \cdot Sp}}.$$

28. A method as claimed in claim 27 wherein step (c) comprises, for each of said sub-segments, reconstructing a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, in step (c), for each of said sub-segments, the plurality of segment images associated therewith respectively have image planes inclined relative to said system axis limited by extreme values $+\delta_{max}$, and $-\delta_{max}$ of said tilt angle δ, according to $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $$\gamma_0 = \arctan\left(\frac{-Sp\bar{\alpha}}{2\pi R_f \sin\bar{\alpha}}\right),$$

and further comprising determining an optimum value $\gamma_{min}$, of said inclination angle γ' for a magnitude of said maximum value of said tilt angle $|\delta_{max}|$ by satisfying an error criterion.

29. A method as claimed in claim 1 wherein step (c) comprises, for each of said sub-segments, reconstructing a plurality $n_{ima}$ of segment images inclined relative to said system axis which have different positions along a z-axis of a Cartesian coordinate system, and wherein, $$n_{ima} = \text{floor}\left[\frac{sM}{p}\right]$$

wherein s is a length of the sub-segment.

30. A method as claimed in claim 29 wherein step (c) comprises, for each of said sub-segments, reconstructing a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis, and wherein, in step (c), for each of said sub-segments, the plurality of segment images associated therewith respectively have image planes inclined relative to said system axis limited by extreme values $+\delta_{max}$, and $-\delta_{max}$ of said tilt angle δ, according to $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $$\gamma_0 = \arctan\left(\frac{-Sp\bar{\alpha}}{2\pi R_f \sin\bar{\alpha}}\right)$$

and further comprising determining the respective tilt angles δ of the inclined image planes according to $$\delta(i) = \delta_{max}\frac{2i - (n_{ima} - 1)}{n_{ima} - 1}.$$

31. A method as claimed in claim 1 wherein each of said segment images has segment image data associated therewith, and comprising the additional step of compressing said segment image data to form compressed data.

32. A method as claimed in claim 31 wherein the step of compressing said segment image data comprises compressing said segment image data to form compressed data exhibiting a non-uniform pixel matrix having resolution in a first direction, proceeding substantially in a direction of a reference projection for the respective sub-segment is higher than in a second direction proceeding substantially orthogonally relative to said reference projection direction.

33. A method as claimed in claim 32 comprising forming said compressed data of pixels having an oblong shape, with each pixel having a longest extent proceeding substantially in said direction of said reference projection direction for that sub-segment.

34. A method as claimed in claim 33 comprising forming said compressed data of rectangular pixels.

35. A method as claimed in claim 33 comprising converting said segment images into said non-uniform pixel matrix.

36. A method as claimed in claim 33 comprising reconstructing said segment images in said non-uniform pixel matrix.

37. A method as claimed in claim 36 wherein said reconstruction of said segment images ensues by back projection in a back-projection direction, and selecting said back-projection direction to substantially coincide with said reference projection direction for that sub-segment.

38. A method as claimed in claim 31 comprising reversing said compression in step (e) to produce said resulting CT image with a uniform pixel matrix.

39. A method as claimed in claim 38 comprising obtaining said pixels of said uniform matrix by interpolation from the pixels of said non-uniform pixel matrix.

40. A method as claimed in claim 38 comprising obtaining said pixels of said uniform matrix by averaging from the pixels of said non-uniform pixel matrix.

41. A computed tomography (CT) apparatus comprising:
 a CT scanner having an x-ray source with a focus and a matrix-like detector array for scanning a subject, having a region exhibiting a periodic motion, with a conical x-ray beam emanating from said focus and detecting said beam, after attenuation by said subject, with said matrix-like detector array while moving said focus along a spiral path around said subject relative to a system axis, said detector array generating output data dependent on radiation from said x-ray beam that is incident thereon;
 a signal acquisition unit adapted for interaction with said subject for obtaining a signal from said subject representing said periodic motion;

a computer supplied with said output data and said signal, said computer dividing said output data, for a segment of said spiral path having a length adequate for reconstructing a CT image, into a plurality of datasets respectively for a plurality of sub-segments of said segment, each of said sub-segments having a length shorter than said length adequate for reconstructing a CT image;

said computer, for each of said sub-segments, reconstructing a plurality of segment images having a plane inclined relative to said system axis from the dataset for that sub-segment;

said computer allocating a z-position on said system axis and a time position with respect to said periodic motion to the respective segment images;

said computer selecting segment images within a range of z-positions and a range of time positions so that respective sub-segments for the selected segment images comprise a total length adequate for reconstruction of a CT image; and said computer combining said selected segment images at least indirectly to form a resulting CT image with respect to a target image plane.

42. A computed tomography apparatus as claimed in claim 41 wherein said periodic motion exhibits phases, and wherein said computer selects segment images with respective sub-segments arising from a single phase of said periodic motion.

43. A computed tomography apparatus as claimed in claim 41 wherein said periodic motion exhibits phases, and wherein said computer selects segment images with respective sub-segments arising from a plurality of phases of said periodic motion.

44. A computed tomography apparatus as claimed in claim 41 wherein said computer directly combines said selected segment images to form said resulting CT image.

45. A computed tomography apparatus as claimed in claim 44 wherein said computer directly combines said selected segment images to form said resulting CT image with respect to a target image plane corresponding to the respective z-positions of the selected segment images.

46. A computed tomography apparatus as claimed in claim 44 wherein said selected segment images have respective z-positions which differ from said target image plane, and wherein said computer reformats said selected segment images into said target image plane before combining said selected segment images to form said resulting CT images.

47. A computed tomography apparatus as claimed in claim 41 wherein said computer, for each of said sub-segments, combines the plurality of segment images to form a partial image with respect to said target image plane, and combines said partial images to form said resulting CT image.

48. A computed tomography apparatus as claimed in claim 47 wherein said computer employs all segment images for a respective sub-segment to form said partial image.

49. A computed tomography apparatus as claimed in claim 48 wherein said resulting CT image represents an image of a slice of said subject, and said computed combines successive, adjacent slices of said subject to produce a resulting CT image of a volume of said subject comprising said slices.

50. A computed tomography apparatus as claimed in claim 49 wherein said successive slices adjoin each other.

51. A computed tomography apparatus as claimed in claim 47 wherein said computer combines said plurality of segment images to form said partial image by interpolation.

52. A computed tomography apparatus as claimed in claim 47 wherein said computer combines said plurality of segment images to form said partial image by averaging.

53. A computed tomography apparatus as claimed in claim 47 wherein said computer combines said plurality of segment images to form said partial image by weighted averaging.

54. A computed tomography apparatus as claimed in claim 43 wherein said computer weights said segment images dependent on a desired reconstruction slice thickness of said partial image.

55. A computed tomography apparatus as claimed in claim 47 wherein said computer selects a number of said segment images for combining to form said partial image dependent on a desired reconstruction slice thickness of said partial image.

56. A computed tomography apparatus as claimed in claim 55 wherein said computer reconstructs said segment images with a smallest possible slice thickness.

57. A computed tomography apparatus as claimed in claim 55 wherein said computer, for each of said sub-segments, selects said plurality of images to be combined for generating said partial image according to:

$$N_M = 2 \cdot \max(z^*, sup_\Phi \Delta z_R) b \cdot N_S.$$

58. A computed tomography apparatus as claimed in claim 47 wherein said computer combines said partial images with respect to a target image plane that intersects said system axis at a right angle.

59. A computed tomography apparatus as claimed in claim 47 wherein said computer combines said partial images to form said resulting CT image by adding said partial images.

60. A computed tomography apparatus as claimed in claim 47 wherein said computer reconstructs at least one of said segment images with a curved image plane.

61. A computed tomography apparatus as claimed in claim 41 wherein said computer, for each of said sub-segments, reconstructs a plurality of said segment images in image planes that are inclined relative to both a first axis, that intersects said system axis at a right angle by an inclination angle γ, and a second axis intersecting each of said first axis and said system axis at respective right angles by a tilt angle δ measured with respect to said system axis.

62. A computed tomography apparatus as claimed in claim 41 wherein said computer divides said output data into sub-segments wherein neighboring sub-segments overlap in overlapping regions, and weighs the output data in said overlap regions so that the respective portions of the output data in said overlapping regions belonging to the neighboring sub-segments in that overlap region have respective weightings which, in combination, add to one.

63. A computed tomography apparatus as claimed in claim 41 wherein said computer, for each of said sub-segments, reconstructs a plurality of segment images inclined relative to said system axis which have different positions along a z-axis of a Cartesian coordinate system.

64. A computed tomography apparatus as claimed in claim 63 wherein said computer, for each of sub-segments, reconstructs a plurality of images respectively in inclined image planes that intersect in a straight line proceeding tangentially relative to that sub-segment, as said plurality of segment images having a plane inclined relative to said system axis.

65. A computed tomography apparatus as claimed in claim 63 wherein said computer, for each of said sub-segments, reconstructs a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis, and wherein, for each of said sub-segments, the plurality of segment images associated therewith respectively have image planes inclined relative to said system axis limited by extreme values $+\delta_{max}$, and $-\delta_{max}$ of said tilt angle $\delta$, according to $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $$\gamma_0 = \arctan\left(\frac{-Sp\bar{\alpha}}{2\pi R_f \sin\bar{\alpha}}\right).$$

66. A computed tomography apparatus as claimed in claim 41 wherein said focus rotates around a rotational axis that coincides with said system axis.

67. A computed tomography apparatus as claimed in claim 41 wherein said focus rotates around a rotational axis that intersects said system axis at a gantry angle $\rho$ and wherein, for each of said sub-segments, the plurality of segment images have respective inclination angles $\gamma'$ according to $$\gamma' = \arctan\frac{Sp\cdot\cos\rho}{\sqrt{4\pi^2\cdot R_f + S^2 p^2 + 4\pi\cdot R_f\cos\alpha\sin\rho\cdot Sp}}.$$

68. A computed tomography apparatus as claimed in claim 67 wherein said computer, for each of said sub-segments, reconstructs a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis, and wherein, for each of said sub-segments, the plurality of segment images associated therewith respectively have image planes inclined relative to said system axis limited by extreme values $+\delta_{max}$, and $-\delta_{max}$ of said tilt angle $\delta$, according to $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

wherein $$\gamma_0 = \arctan\left(\frac{-Sp\bar{\alpha}}{2\pi R_f \sin\bar{\alpha}}\right),$$

and further comprising determining an optimum value $\gamma_{min}$, of said inclination angle $\gamma'$ for a magnitude of said maximum value of said tilt angle $|\delta_{max}|$ by satisfying an error criterion.

69. A computed tomography apparatus as claimed in claim 41 wherein said computer, for each of said sub-segments, reconstructs a plurality $n_{ima}$ of segment images inclined relative to said system axis which have different positions along a z-axis of a Cartesian coordinate system, and wherein, $$n_{ima} = \text{floor}\left[\frac{sM}{p}\right]$$

wherein s is a length of the sub-segment.

70. A computed tomography apparatus as claimed in claim 69 wherein said computer, for each of said sub-segments, reconstructing a plurality of said segment images in image planes that are inclined relative to both a first axis, that intersects said system axis at a right angle by an inclination angle $\gamma$, and a second axis intersecting each of said first axis and said system axis at respective right angles by a tilt angle $\delta$ measured with respect to said system axis, and wherein, for each of said sub-segments, the plurality of segment images associated therewith respectively have image planes inclined relative to said system axis limited by extreme values $+\delta_{max}$, and $-\delta_{max}$ of said tilt angle $\delta$, according to $$\pm\delta_{max} = \arctan\left(\frac{-\frac{bM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right) \text{ wherein}$$

$$\gamma_0 = \arctan\left(\frac{-Sp\bar{\alpha}}{2\pi R_f \sin\bar{\alpha}}\right)$$

and further comprising determining the respective tilt angles $\delta$ of the inclined image planes according to $$\delta(i) = \delta_{max}\frac{2i - (n_{ima} - 1)}{n_{ima} - 1}.$$

71. A computed tomography apparatus as claimed in claim 41 wherein each of said segment images has segment image data associated therewith, and wherein said computer has a compression stage compressing said segment image data to form compressed data.

72. A computed tomography apparatus as claimed in claim 71 wherein said compression stage compresses said segment image data to form compressed data exhibiting a non-uniform pixel matrix having resolution in a first direction, proceeding substantially in a direction of a reference projection for the respective sub-segment is higher than in a second direction proceeding substantially orthogonally relative to said reference projection direction.

73. A computed tomography apparatus as claimed in claim 72 wherein said compression stage forms said compressed data of pixels having an oblong shape, with each pixel having a longest extent proceeding substantially in said direction of said reference projection direction for that sub-segment.

74. A computed tomography apparatus as claimed in claim 73 wherein said compression stage forms said compressed data of rectangular pixels.

75. A computed tomography apparatus as claimed in claim 73 wherein said computer converts said segment images into said non-uniform pixel matrix.

76. A computed tomography apparatus as claimed in claim 73 wherein said computer reconstructs said segment images in said non-uniform pixel matrix.

77. A computed tomography apparatus as claimed in claim 76 wherein said computer reconstructs said segment images ensues by back projection in a back-projection direction, and selects said back-projection direction to substantially coincide with said reference projection direction for that sub-segment.

78. A computed tomography apparatus as claimed in claim 72 wherein said computer reverses said compression to produce said resulting CT image with a uniform pixel matrix.

79. A computed tomography apparatus as claimed in claim 78 wherein said computer obtains said pixels of said uniform matrix by interpolation from the pixels of said non-uniform pixel matrix.

80. A computed tomography apparatus as claimed in claim 78 wherein said computer obtains said pixels of said uniform matrix by averaging from the pixels of said non-uniform pixel matrix.

* * * * *